United States Patent [19]

Salyer

[11] Patent Number: 5,254,380
[45] Date of Patent: Oct. 19, 1993

[54] DRY POWDER MIXES COMPRISING PHASE CHANGE MATERIALS

[75] Inventor: Ival O. Salyer, Dayton, Ohio

[73] Assignee: University of Dayton, Dayton, Ohio

[21] Appl. No.: 48,324

[22] Filed: Mar. 17, 1993

Related U.S. Application Data

[62] Division of Ser. No. 835,854, Feb. 2, 1992, Pat. No. 5,211,949, which is a division of Ser. No. 462,365, Jan. 9, 1990, Pat. No. 5,106,520.

[51] Int. Cl.$^5$ .................. B29D 22/00; B32B 1/00; A47G 23/04; F24H 7/00
[52] U.S. Cl. .................. 428/35.7; 428/36.2; 428/36.4; 428/36.92; 428/402; 524/493; 126/246; 126/400
[58] Field of Search .............. 428/36.4, 36.2, 402, 428/36.92, 35.7; 126/400, 246; 252/70; 524/493

[56] References Cited

U.S. PATENT DOCUMENTS

| | | |
|---|---|---|
| 3,603,106 | 9/1971 | Ryan et al. . |
| 3,639,189 | 2/1972 | Hartman . |
| 3,823,089 | 7/1974 | Ryan et al. . |
| 4,003,426 | 1/1977 | Best et al. . |
| 4,008,170 | 2/1977 | Allan ............................ 252/192 |
| 4,045,515 | 8/1977 | Isaka et al. . |
| 4,182,398 | 1/1980 | Salyer . |
| 4,233,960 | 11/1980 | Johnson ........................ 126/400 |
| 4,253,983 | 3/1981 | Blanie ............................ 252/70 |
| 4,259,198 | 3/1981 | Kreibich et al. . |
| 4,259,401 | 3/1981 | Chahroudi et al. ........... 126/429 |
| 4,273,667 | 6/1981 | Kent et al. .................... 252/70 |
| 4,294,078 | 10/1981 | MacCracken ................. 62/59 |
| 4,367,788 | 1/1983 | Cordon ......................... 165/53 |
| 4,463,799 | 8/1984 | Takahashi et al. . |
| 4,470,917 | 9/1984 | Hawe et al. .................. 252/70 |
| 4,504,402 | 3/1985 | Chen et al. . |
| 4,505,953 | 3/1985 | Chen et al. . |
| 4,513,053 | 4/1985 | Chen et al. . |
| 4,545,916 | 10/1985 | Chalk ........................... 252/70 |
| 4,561,989 | 12/1985 | Wada et al. .................. 252/70 |
| 4,567,877 | 2/1986 | Sepahpur ..................... 126/400 |
| 4,711,813 | 12/1987 | Salyer ........................... 428/402 |
| 4,715,978 | 12/1987 | Yano et al. ................... 252/70 |
| 4,777,931 | 10/1988 | Ziegler et al. ................ 126/246 |
| 4,982,722 | 1/1991 | Wyatt ........................... 126/400 |
| 4,983,798 | 1/1991 | Eckler et al. ................. 126/246 |
| 5,052,369 | 10/1991 | Johnson ....................... 126/400 |
| 5,125,391 | 6/1992 | Srivastava et al. ........... 126/246 |
| 5,211,949 | 5/1993 | Salyer ........................... 428/402 |

FOREIGN PATENT DOCUMENTS

| | | |
|---|---|---|
| 0022717 | 1/1981 | European Pat. Off. . |
| 3045842 | 7/1982 | Fed. Rep. of Germany . |
| 2368529 | 6/1978 | France . |
| 0042380 | 4/1979 | Japan . |
| 0142276 | 8/1984 | Japan . |
| 0170180 | 9/1984 | Japan . |
| 0232164 | 12/1984 | Japan . |
| 0086188 | 5/1985 | Japan . |
| 0086191 | 5/1985 | Japan . |

*Primary Examiner*—Herbert J. Lilling
*Attorney, Agent, or Firm*—Killworth, Gottman, Hagan & Schaeff

[57] ABSTRACT

Free flowing, conformable powder-like mix of silica particles and a phase change material (p.c.m.) is disclosed. The silica particles have a critical size of about $7 \times 10^{-3}$ to about $7 \times 10^{-2}$ microns and the pcm must be added to the silica in an amount of 80 wt. % or less pcm per combined weight of silica and pcm. The powder-like mix can be used in tableware items, medical wraps, tree wraps, garments, quilts and blankets, and in cementitious compositions of the type in which it is beneficial to use a pcm material. The silica-pcm mix can also be admixed with soil to provide a soil warming effect and placed about a tree, flower, or shrub.

10 Claims, 5 Drawing Sheets

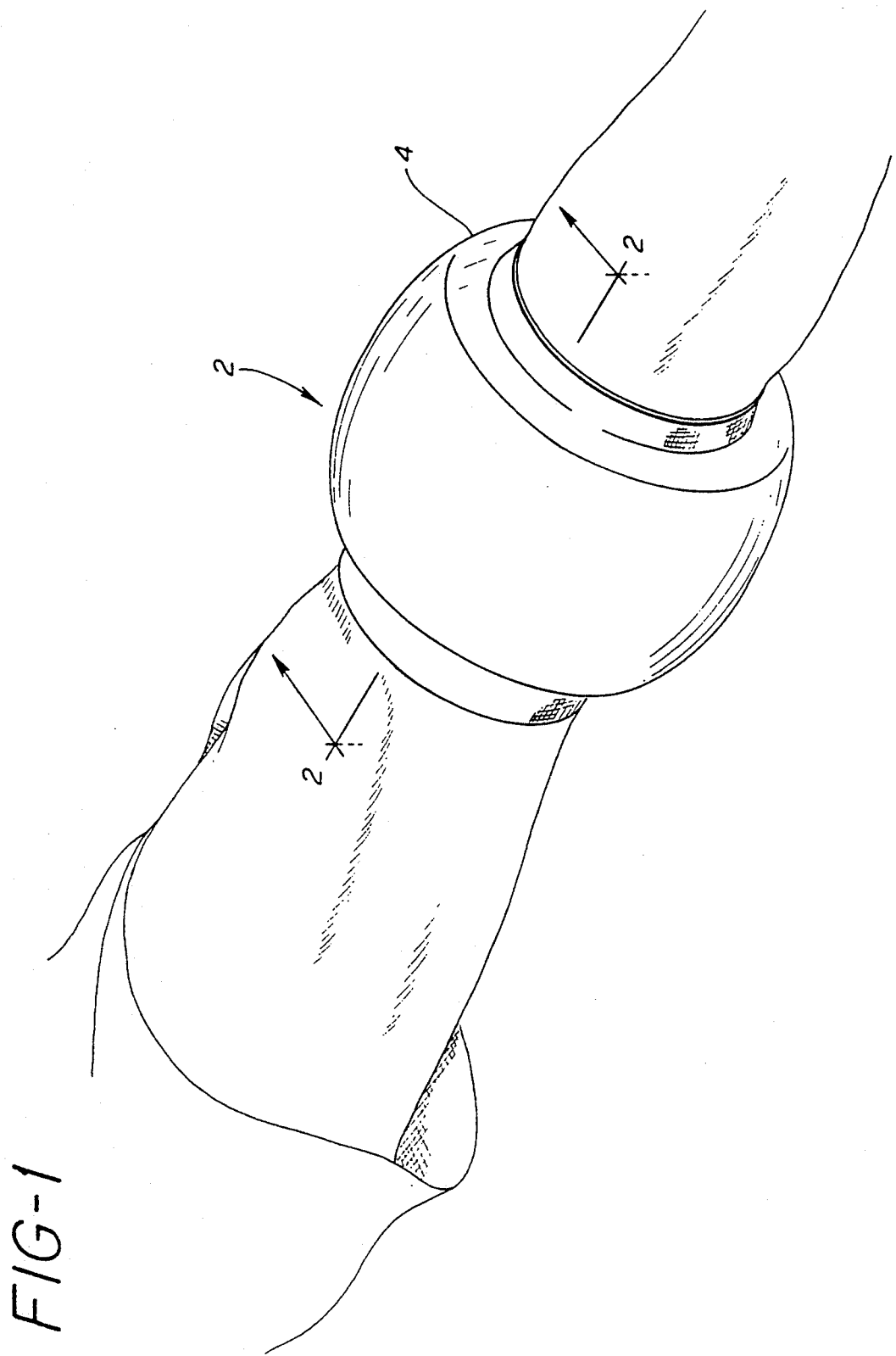

DRY POWDER MIXES COMPRISING PHASE CHANGE MATERIALS

GOVERNMENT RIGHTS

The Government has rights in this invention pursuant to Contract No. DE-FG03-86SF16308 awarded by the U.S. Department of Energy.

This is a division of application Ser. No. 835,854, filed Feb. 2, 1992 now U.S. Pat. No. 5,211,947 as a division of application Ser. No. 462,365, filed Jan. 9, 1990, now U.S. Pat. No. 5,106,520.

FIELD OF THE INVENTION

This invention relates to a dry, freely flowing powder mix comprising a phase change material.

BACKGROUND OF THE INVENTION

Phase change materials may be repeatedly converted between solid and liquid phases and utilize their latent heat of fusion to absorb, store and release heat or cool during such phase conversions.

These latent heats of fusion are greater than the sensible heat capacities of the materials. For example, in phase change materials, the amount of energy absorbed upon melting or released upon freezing is much greater than the amount of energy absorbed or released upon increasing or decreasing the temperature of the material at an increment of 1° C.

Upon melting and freezing, per unit weight, a phase change material (P.C.M.) absorbs and releases substantially more energy than a sensible heat storage material that is heated or cooled to the same temperature range. In contrast to a sensible heat storage material that absorbs and releases energy essentially uniformly over a broad temperature range, a phase change material absorbs and releases a large quantity of energy in the vicinity of its melting/freezing point.

Phase change materials capable of storing and releasing thermal energy have found many applications in building structures, road base materials, beverage and food containers, medical wraps, and textile applications such as garments. One of the basic problems, however, in the use of solid-to-liquid PCMs for control of temperature, is containment. That is, for heat transfer efficiency as well as safety purposes, it is undesirable to have a thick block or agglomeration of solid phase PCM below the PCM melting point. Similarly, when above the melting point, PCM in liquid phase can be problematic. For instance, building panels containing liquid phase PCM have proven deficient. In one such PCM-containing panel, carpenters reported that a liquid phase PCM leaked out of the panel when nails were driven through it.

In those situations in which medical hot or cold packs containing PCMs are used, a solid phase agglomerate of PCM below its melting point renders the structure unwieldy and incapable of conforming about the required body part to achieve the desired heating or cooling function.

Accordingly, it is an object of the invention to provide a conformable, powder-like PCM-matrix composite that will not liquefy upon heating of the PCM above its melting point and will not form a rigid solid at temperatures below the melting point. In other words, it is desirable to find a new method of containment for the PCM wherein, when above or below its melting point, the PCM-matrix structure will be in the form of a soft, conformable configuration like a sand pack.

SUMMARY OF THE INVENTION

I have found that a very small size silica filler may be used as a matrix for the PCM. This silica filler has particle sizes on the order of about 0.007 to 0.07 microns in diameter and is capable of absorbing five to ten times its weight of liquid PCM. The silica filler is literally stirred into the liquid PCM at a temperature that is above the melting point of the PCM. At combinations of PCM/silica filler of 90/10-85/15 (weight) a gel composition is obtained. However, when mixed at 80/20 PCM/silica filler and at lower PCM content, a free-flowing powder is obtained that remains free flowing above and below the melting temperature of the PCM. This type of structure is especially desirable for hot and cold medical wrap applications, but is of interest in other applications such as for citrus tree wraps, tableware, building structures, soil admixtures, garments, blankets, quilts, etc.

In those situations in which the PCM/silica mix is to be used as a hot medical wrap, it is desirable to provide a microwavable package containing the mix. To enhance this capacity, polar additives may be added to the mix to absorb microwave energy effectively or the PCM itself maybe a polar compound such as a high molecular weight (i.e., $\geq 1,000$) polyethyleneglycol material.

A variety of different PCM materials may be used in the silica-PCM mixture as long as the melting and freezing temperatures thereof fall within a broad range of between about $-20°$ to about $140°$ C. The lower melting PCMs are useful for medical therapy cold pack, citrus tree frost protection and soil admixtures, with the higher melting PCMs being useful for medical therapy heat packs, tableware, etc. It is preferred that the PCM have a latent heat of fusion of about 30 cal./gram or higher.

PRIOR ART

The broad idea of using silica as a suspension medium for PCMs in building blocks is not new. For instance, see U.S. Pat. No. 4,259,401 (Chahrowudi et al) wherein this concept is disclosed at column 21, line 60 et seq.

A microwavable heat storage food container comprising wet sand as a thermal storage medium is disclosed in U.S. Pat. No. 4,567,877 (Sepahpur). Of further possible interest is U.S. Pat. No. 4,367,788 (Cordon) which is directed toward the use of PCM materials such as glauber's salt that are absorbed by porous perlite materials. Other patents of possible interest are U.S. Pat. No. 4,294,078 (MacCracken) and U.S. Pat. No. 4,711,813 (Salyer).

The prior art however does not suggest utilization of the combination of specific particle size silica and PCM/silica weight ratios herein required in order to result in a dry, conformable, powder-like, PCM containing composition that may be useful in widespread environments.

DETAILED DESCRIPTION OF THE PREFERRED EMBODIMENT

In accordance with the invention, a dry powder-like PCM-silica mix is provided that may be used for: medical hot and cold pack applications, as a wrap for citrus trees, or in admixture with soil to protect trees or plants implanted therein, building structure applications such as in plasterboard, and food and tableware accessory items, etc.

The particle size of the silica is critical. I have found that sub-micron, ultra fine particle size silicas on the order of about $7 \times 10^{-3}$ to about $7 \times 10^{-2}$ microns (in diameter) can be manually mixed in a solution of phase change material within a critical addition range. That is, the ultra-fine silica should be added to the phase change material an amount of about 80% PCM (weight PCM based on total weight of PCM and silica in mix) or less. If more than about 80% of the PCM is added, a gel-like mixture is provided. However, at about 80/20 PCM:silica, a free-flowing powder is obtained that remains free-flowing both above and below the melting temperature of the PCM. This type of structure is especially desirable for hot and cold medical wraps, but is of interest for other applications as well (such as in citrus tree wraps, tableware, garments, blankets).

The preferred addition range for the PCM is from about 80%-50% (by weight based upon total weight of the composite, i.e., silica-PCM mixture). For convenience in mixing, I have usually added the dry silica to liquid PCM (i.e., PCM maintained at a temperature higher than its melting point). However, the reverse addition of PCM to silica can also be accomplished with suitable equipment to prevent aerosolization of the finely divided silica.

As to the silica materials which may be used, these are sub-micron size silicas having particle sizes on the order of 0.007 to about 0.07 microns. The finely divided silicas that have been used successfully to date have come from commercially available pigmentary grades of silica such as are used as reinforcing filler in rubbers. These pigmentary grades of silica are orders of magnitude smaller in size than sand particles and have other important differences as well.

Typically, these sub-micron silicas are made by one of two different processes. For example, fumed silica is made by hydrolysis of silicon tetrachloride vapor in a hydrogen/oxygen flame. Precipitated silicas are made from an alkaline silicate (e.g., sodium silicate) that is precipitated with a mineral acid or metal salt.

Both procedures produce a small spherical particle with multiple hydroxyl groups located at the surface and a three-dimensional chain-like structure (as in carbon black). The chain structure is thought to be very important to the reinforcing, gel formation, and other properties of the silicas. The surface area of the silicas may range from 50 square meters/gram to 500 m² or even higher.

Exemplary silicas include the "Cab-o-Sil ®" series of fumed silicas available from Cabot Corporation, Tuscola, Ill., and the "Aerosil ®", FK series, Sipernat ® series, Ultrasil ® and Quso ® series silicas available from DeGussa. Hi Sil ® precipitated silicas from PPG may also be mentioned as being useful. At present, the preferred silica is Cab-o-Sil ® MS-7SD fumed silica from Cabot. This particular silica has the following physical characteristics.

| | |
|---|---|
| Surface Area (m²/g) | 175-225 |
| pH (4% Aqueous Dispersion) | 3.7-4.3 |
| Density (lbs./cu. ft.) | 9-11 |
| Wt. % Moisture | 1.5 max |
| Silica content | 99.8 min |
| Specific Gravity | 2.2 |
| Refractive Index | 1.46 |
| Color | White |
| X-Ray Form | Amorphous |

As to the PCMs that can be used, crystalline alkyl hydrocarbons having a chain length of $C_{14}$ and greater are preferred for most situations. Other PCMs that may be mentioned include water, glycerine, crystalline fatty acids, crystalline fatty acid esters, crystalline alicyclic hydrocarbons, crystalline aromatic compounds, hydrated salts (Glauber's Salt preferred), the clathrates, semi-clathrates, gas clathrates, polyethylene glycol, and halogen-terminated alkyl hydrocarbons.

Suitable clathrates include those which consist of either a noble gas (i.e., the gas clathrates) or a non-polar halocarbon which forms hydrates in as little as 10% concentration. The chlorofluorocarbon clathrates tend to be relatively expensive and are, therefore, not preferred. Additionally, some specific chlorofluorocarbons (e.g., Freon 11, 12, etc.) are also suspected to contribute to depletion of the earth's ozone shield and are undesirable for this reason as well.

Promising clathrate pcms also include the quaternary amine salts with halogen or other acids (clathrates or semi-clathrates). These hydrates are pseudo compounds, wherein the crystals of "ice" are able to host organic molecules (of specific composition) in nearly spherical cages of two different sizes. If only the larger of the two cages is occupied by the guest molecules, the pcm may contain 33 or more molecules of water. If both cages are occupied by guest molecules, the PCM will contain about 17 molecules of water. In either case, the water content in these clathrate and semi-clathrate pcms is much higher than in some of the salt hydrates such as sodium sulfate decahydrate.

Nearly all hydrated salts can be employed, with various degree of suitability, as PCM. The only such materials which are wholly unsuitable are those which decompose, rather than melt. Marginally suitable hydrated salts are those which melt incongruously, those with low heats of fusion, and those with melting points which lie outside (generally far above) desired temperature ranges. Nevertheless, there are a wide variety of meltable hydrated salts with high heat of fusion and useable melting points; and many of these satisfy stringent cost requirements. The preferred hydrated salts are those which are formed primarily from the combination of positive ions of sodium, potassium, calcium, ammonium and iron with negative ions of acetate, silicate, chloride, nitrate, mono, di, and tri basic phosphate, mono and di basic carbonate and mono and di basic sulphate. Other ions may be added to the above combinations in small quantities, (although they are more expensive) in order to adjust melting point or to obtain other desired properties. Virtually all such combinations will function in the desired manner; and most have melting points in the useful range, for example: $Fe_2O_3.4SO_3.9H_2O$, $NaNH_4SO_4.2H_2O$, $NaNH_4HPO_4.4H_2O$, $FeCl_3.2H_2O$, $Na_3PO_4.12H_2O$, $Na_2SiO_3.5H_2O$, $Ca(NO_3)_2.3H_2O$, $K_2HPO_4.3H_2O$, $Na_2SiO_3.9H_2O$, $Fe(NO_3)_3.9H_2O$, $K_3PO_4.7H_2O$, $NaHPO_4.12H_2O$, $CaCl_2.6H_2O$ and $Na_2SO_4.10H_2O$, $Na(CH_3COO).3H_2O$. The specific melting point desired is obtained by varying the degree of hydration and by alloying it to form binary or trinary eutectics.

As above noted, the crystalline alkyl hydrocarbons having a carbon chain of about 14° C. atoms or greater are preferred. These waxes are commercially available under a host of trademarks. For instance, these commercially available waxes include: Shellwax ® 100 (MP 42°-44° C.), Shellwax ® 120 (MP 44°-47° C.), Shellwax ® 200 (MP 52°-55° C.), Shellwax ®300 (MP 60°-65° C.) all of which are products of Shell Oil Co.; Boron R-152 (MP 65° C.) a product of Standard Oil of Ohio (SOHIO); Union SR-143 (MP about 61° C.) a product of Union Oil Co.; Witco 128 (MP about 53° C.) Witco LLN, Witco 45A, Witco K-61, Witco K-51, and Witco 85010-1 all products of Witco Corporation (Kendall Division); Aristowax ®143 (MP 34°-61° C.), and Paraffin 150 (MP about 61° C.). These waxes have heats of fusion greater than 30 cal/g and by comparison to other phase change materials, they are inexpensive.

One group of waxes for use in the present invention includes commercially available mixtures of crystalline alkyl hydrocarbons. These mixtures of alkyl hydrocarbons are obtained at low cost as by-products of petroleum refining. Typically, these are blends of alkyl hydrocarbons which differ by no more than 4 or 5 carbon atoms. A typical example is Witco 45A which contains about 21% C-18, 33% C-19, 26% C-20; 11% C-21 hydrocarbon, and the balance higher and lower hydrocarbons. Because they are inexpensive, they can be incorporated into the silica-pcm composite at minimal additional expense and, at the same time, provide high savings in terms of reduced energy costs.

While these waxes are mixtures they exhibit one melting freezing point which is the average of the melting freezing points of the constituents. Some blends for passive heating and cooling have a melting and freezing point in the range of 24° to 33° C. Some blends for passive cool storage have a melting and freezing point in the range of 0° to 33° C. In many applications, the blends will be relied upon for both heating and cooling and will be characterized by having both the melting and a freezing point in the range of 20° to 25° C.

Ultra pure alkyl hydrocarbons C-14 to C-22 and higher are also available at a premium cost. These may have higher heats of fusion and crystallization (e.g., 55-60 cal/g) than the low-cost mixtures described above. These ultra pure alkyl hydrocarbons are also useful in the present invention for critical applications requiring maximum storage capacity in the minimum volume of space.

Another consideration in the selection of waxes used in the present invention is the difference between the melting and freezing points. The alkyl hydrocarbons are self-nucleating and thus melt and freeze congruently. Thus, when heated or cooled at rates of 2 C/min. or less, the melting and freezing temperatures substantially coincide.

Additionally, the halogen terminated alkyl hydrocarbons can be useful as a pcm and also provide fire retardancy.

When the powder-like silica/pcm mixture is to be used for medical hot wrap applications, it is desirable to heat the mix via microwave or other dielectric heating means. In such cases, a polar pcm such as water, glycerine, ethylene glycol, a high molecular weight (i.e., greater than 1,000) polyethylene glycol, the clathrates, semi-clathrates, gas-clathrates and hydrates may be used.

Alternatively, if a microwavable product is desired, a non-polar pcm such as the crystalline long chain ($C_{14}$ and greater) alkylhydrocarbons, crystalline fatty acids, crystalline fatty acid esters, crystalline alicyclic hydrocarbons and crystalline aromatic hydrocarbons can be used provided they are used conjointly with polar compounds such as water, ethylene glycol, glycerine, polyethylene glycol, and ivory liquid, etc. Such polar compounds should be added to the silica-pcm composite in an amount of from 5-25 wt. %, preferably 5-10 wt. % (based upon the total weight of the silica/pcm/polar compound combination).

In those end use environments in which high humidity conditions are encountered, the silicas tend to have a greater affinity for water than for the preferred alkyl hydrocarbon PCM. This limitation is important in attempting to add the silica-liquid alkyl hydrocarbon ($C_{14}$ and greater) to a wet mix of plaster or concrete. In these cases, preliminary tests have demonstrated a partial separation of the PCM from the hydrophilic silica that comprises a multiplicity of surface hydroxyl groups. However, to minimize such phase separation problems, surface modification of the hydrophilic silicas to form hydrophobic silica appears promising. For example, the fumed or precipitated ultra-fine silicas are normally hydrophilic. However, when modified by treatment with a suitable coupling agent, for instance, dimethyldichlorosilane, divinyldichlorosilane, hexamethyldisilazane, etc., a hydrophobic silica having different properties from the untreated base silica is formed. Although applicant is not to be bound to any particular theory of operation, it is thought that the treatment with the coupling agent replaces many of the available surface OH groups on the silica particles with organic moieties such as alkyl or aryl groups. This renders the silica hydrophobic.

One such "surface modified" silica is sold by Cabot under the "Cab-o-Sil ® 610" trademark. This hydrophobic silica is therefore highly preferred in those situations in which the silica-pcm powder mix will be subjected to high humidity or aqueous environments such as those that may be found when the mix is to be used in building structures, for example, in cementitious mixes such as in plaster, plasterboard and concrete mixes. Further, the hydrophobic silicas would be used in those situations in which the silica-pcm powder mix is to be admixed with soil so as to provide controlled heat release to plants or trees implanted in the soil.

"Cab-o-Sil ® 610" has the following physical characteristics:

| Appearance | Fluffy white powder |
|---|---|
| surface area (BET)($m^2$/g) | 120 ± 15 |
| pH[1] | 4.0-5.0 |
| Carbon (wt. %) | 0.85 ± 0.15 |
| Bulk Density (lbs./cu.ft.) | ≈3.0 |
| Loss on Heating[2] (wt. %) | 0.5 |

[1] 4 g in 100 g of 80/20 isopropanol/water by weight
[2] 2 hours at 110° C.

The surface structure of "Cab-o-Sil ® 610" is thought to be as follows:

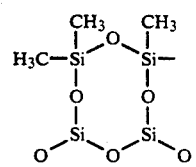

Another exemplary hydrophobic silica is available from Cabot under the "Cab-o-Sil" 720 trademark. This hydrophobic silica has had its surface modified via reaction with hexamethyldisilazane and is thought to have the surface structure of:

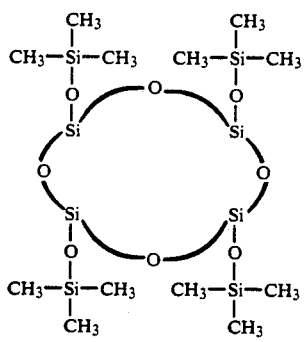

Other exemplary hydrophobic silicas include Aerosil ® R 972 and Aerosil ® R 974, available from Degussa.

As used herein in the specification and claims, hydrophobic silica is used to refer to a silica that will not exhibit separation of pcm from the pcm-silica powder mix when the mix is subjected to water or high humidity conditions (i.e., $\geq 90\%$ R.H.).

DRAWINGS

The invention will now be further explained in conjunction with the attached drawings. In the drawings:

FIG. 1 is a diagrammatic view of a medical wrap utilizing the silica-pcm powder-like composite of the invention;

Figure 2A:
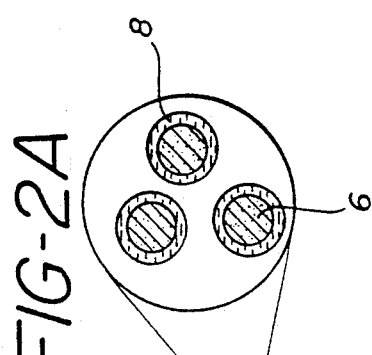
FIG. 2A is a magnified cut-away view showing the single phase nature of the silica/pcm combination.
Figure 2:
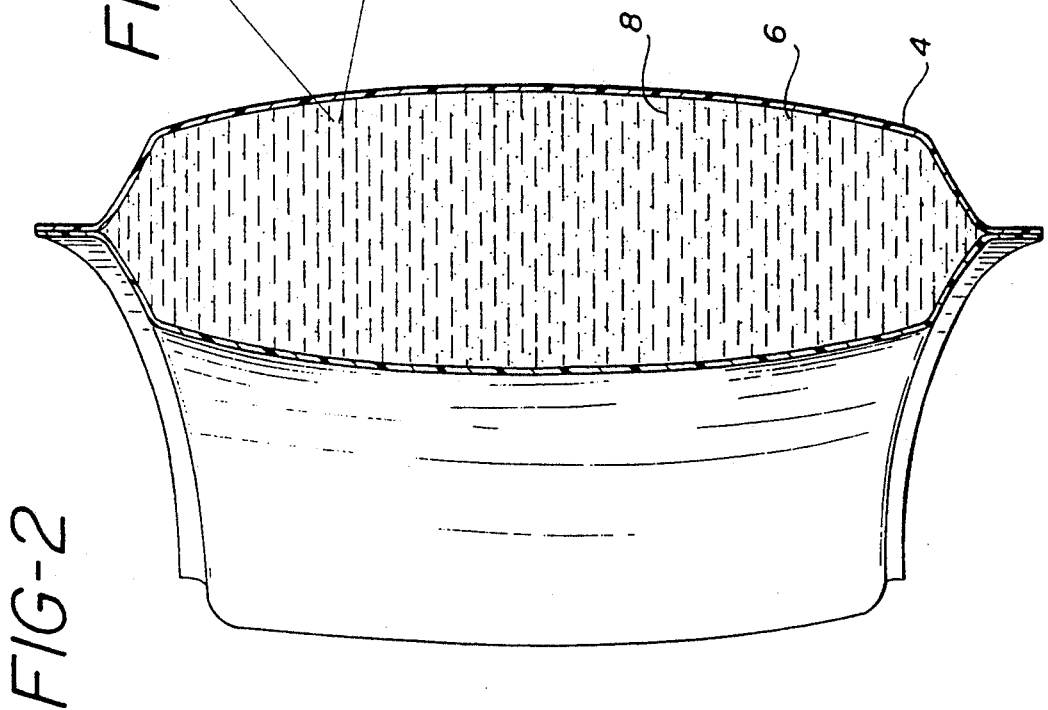
FIG. 2 is a sectional view taken along the lines and arrows 2—2 shown in FIG. 1.

Turning now to the drawings and to FIGS. 1 and 2 thereof, there is shown medical wrap 2, specifically a knee joint wrap comprising outer envelope 4, formed from a liquid impervious polymer such as a butadieneacrylonitrile copolymer, a polyester such as polyethylene terephthalate or vinyl polymer such as plasticized polyvinyl chloride, plasticized polyvinylidene chloride, low and high density polyethylene and ethylenevinylacetate copolymers. Housed within the liquid impervious outer envelope is a powder-like mix comprising silica 6, as specified supra., and a pcm material 8. The medical wrap 2 may also comprise fastener means such as "Velcro" strips (not shown) to provide for attachment of the wrap around the desired anatomical body part. In this case, since outer envelope 4 is liquid impervious, it is not necessary to utilize the hydrophobic version of the ultra-fine silica particles. Additionally, for such medical wrap applications, it is desirable that the pcm have a melting and freezing point within the range of 0°-60° C.

With respect to FIG. 2A, it can be seen that the silica/pcm combination provides a single phase mixture wherein the silica particles 36 are coated with the pcm 38 material.

Figure 3:
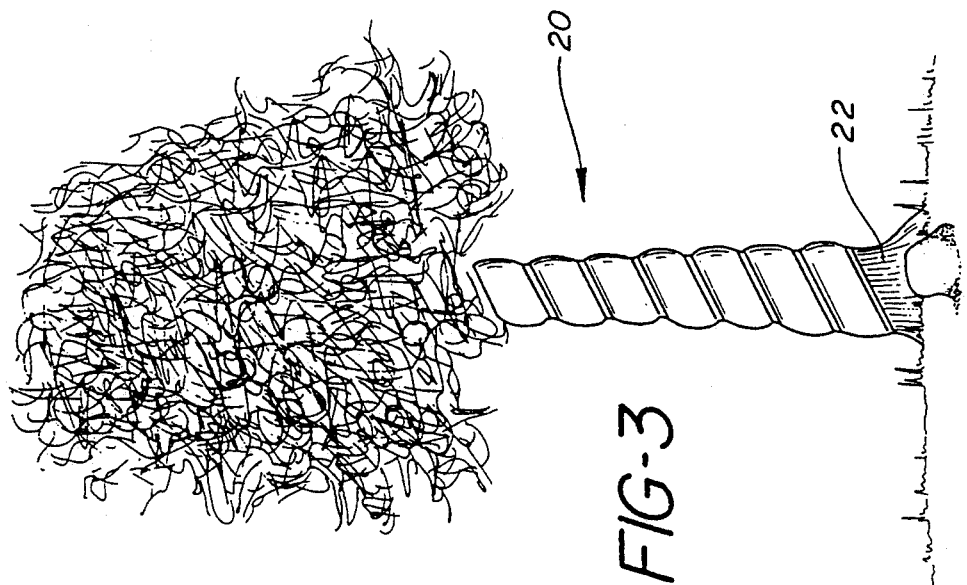
FIG. 3 is a diagrammatic view of a citrus tree wrap incorporating the silica-pcm powder-like composite of the invention.

FIG. 3 depicts tree wrap 20 wrapped around the base of citrus tree 22. The outer envelope of the tree wrap is similar to envelope 4 shown in FIGS. 1 and 2. The silica-pcm conformable free-flowing powder-like mix comprising silica particles and pcm is mixed and encased within the envelope in the same manner as shown for the medical wrap in FIGS. 1 and 2. The melting and freezing point of the tree wrap pcm should be from about 0°-20° C.

Instead of using a wrap, it is possible to mix the silica-pcm powder-like composite with the soil surrounding plants, bushes, flowers, etc., to provide warming heat energy protection thereto. In this case, the melting point and freezing point of the pcm should ideally be in the range of about 0°-25° C.

Figure 4:
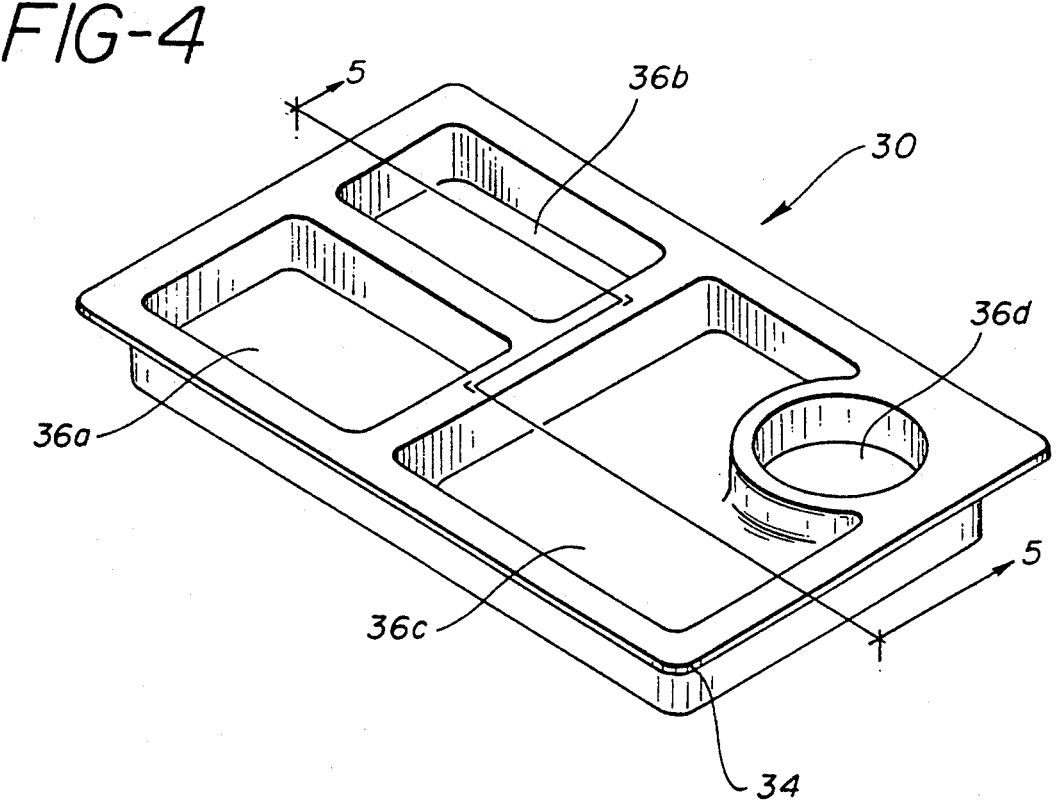
FIG. 4 is a diagrammatic view of a tableware item, a dinner serving tray, utilizing the silica-pcm powder-like composite of the invention.
Figure 5:
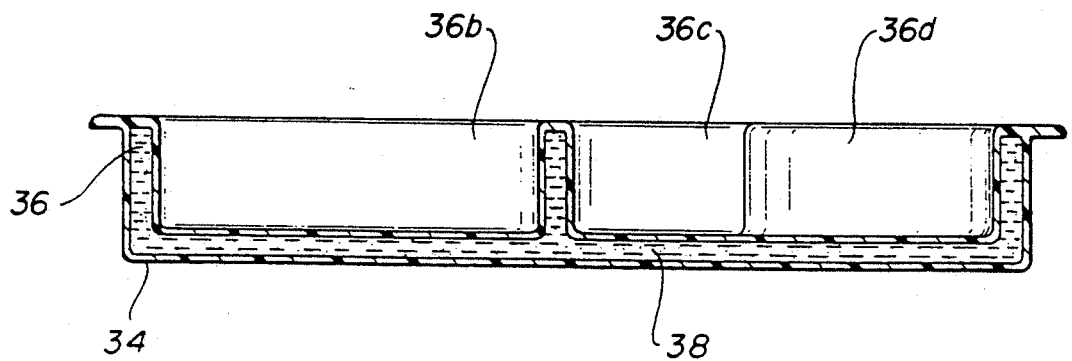
FIG. 5 is a sectional view taken along the lines and arrows 5—5 in FIG. 4.

FIGS. 4 and 5 depict a tableware item, a dinner serving tray 30 of the type used by airlines, etc., that incorporates the free-flowing powder-like pcm material disposed therein. Here, serving tray 30, comprises a plastic housing 34 that is filled with the silica 36 pcm 38 mix. The tray 30 comprises a plurality of compartments 36a-d to act as receptacles for food and a beverage container. For this particular end-use, a melting point and freezing point for the pcm should be chosen in the range of about 20°-80° C.

Figure 6:
FIG. 6 is a diagrammatic view of a garment, a vest, that incorporates the silica-pcm powder-like composite of the present invention.
Figure 7:
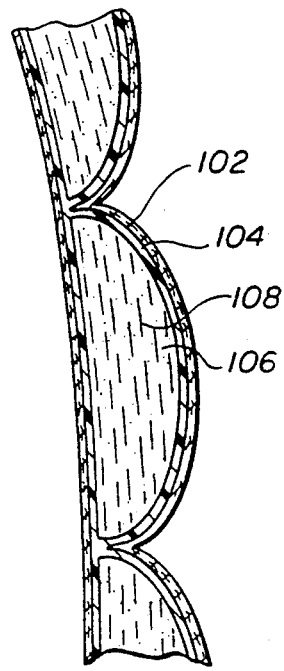
FIG. 7 is a cross-sectional view taken along the lines and arrows 7—7 shown in FIG. 6.

Turning now to FIGS. 6 and 7 of the drawings, a textile garment, here a vest 100 is shown that is provided with a plurality of pouch portions 102 that may be sewn in the garment or attached thereto by other conventional means. In each pouch 102 is provided a polymeric, liquid impervious enclosure 104 that is filled with the ultra-fine silica particles 106 and pcm material 108. In such manner, a pcm containing textile garment is provided wherein the pcm is chosen so as to release heat to the wearer at a desired temperature, usually from 0°-60° C.

Figure 8:
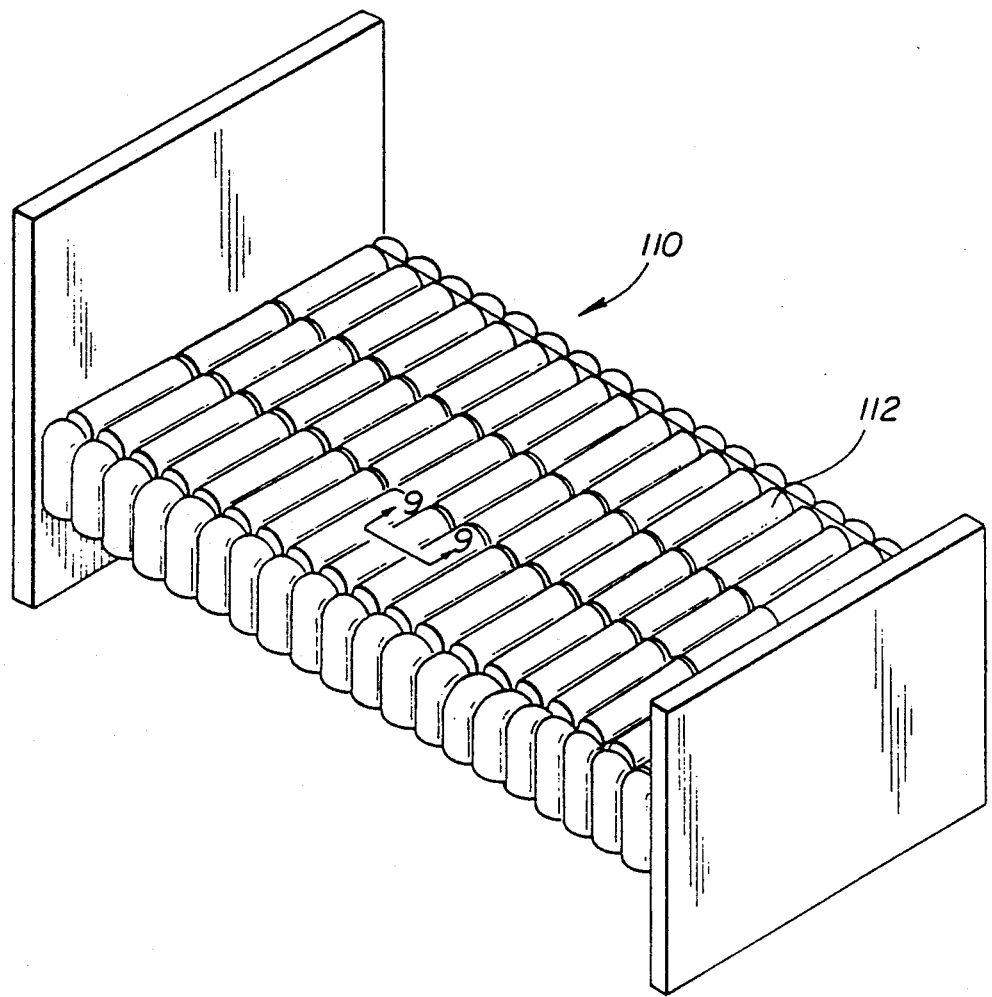
FIG. 8 is a diagrammatic view of a quilt incorporating the silica-pcm powder-like composite of the invention.
Figure 9:
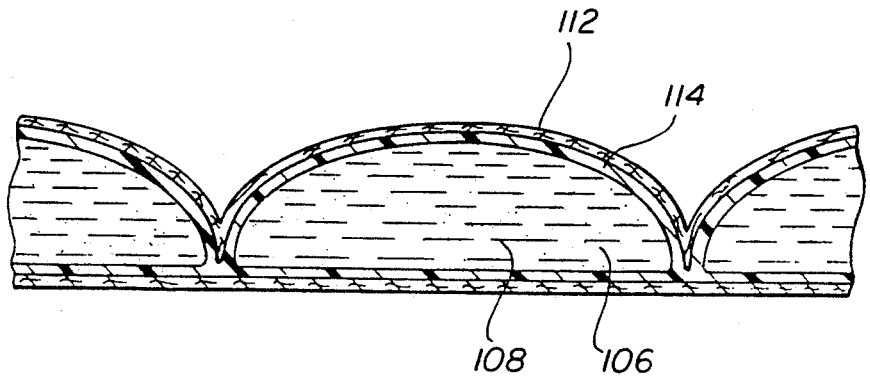
FIG. 9 is a cross-sectional view taken along the lines and arrows 9—9 shown in FIG. 8.

FIGS. 8 and 9 illustrate application of the invention to a blanket or quilt 110. Again, pouches 112 formed between the interstices of the layers of the fabric sheet are lined with a polymeric liquid impervious enclosure 114 that is filled with the pcm 108 and ultra-fine silica 106. The pcm can be chosen so as to liberate heat at desired temperatures, normally from 0°-60° C.

In accordance with the above, it is apparent that the ultrafine particle size silica provides a convenient carrier for the pcm. The fact that the pcm-silica powder mix readily conforms to different shapes is of benefit when the mix is used as a medical hot or cold pack. The dry blend minimizes pcm leakage problems that may otherwise occur. Use of hydrophobic silica in combination with non-polar PCM provides solution to a phase separation problem otherwise encountered in high humidity environments.

The silica-pcm mix may also be enhanced by the use of an antioxidant in the formulation. Typically, the antioxidant will be needed only when the crystalline alkyl hydrocarbon pcm or a polar organic pcm such as ethylene glycol, polyethyleneglycol or glycerine is employed. The antioxidants should be added, when used, in an amount of from 0-1% (weight) based on the weight of the pcm. Exemplary antioxidants include the well-know hindered phenol materials and aromatic amines. Preferred antioxidants include BHA (butylated hydroxy anisole), Santowhite crystals (i.e., 4,4'-thiobis(6-tert-butyl-m-cresol)) and Santowhite powder (i.e., 4,4'-isopropylidene bis(6-tert-butyl-m-cresol). The Santowhite products are available from Monsanto.

It should be noted that the polar pcms such as the hydrates, clathrates, semi-clathrates, gas clathrates, water, glycerine, and polyethylene glycol will not properly wet hydrophobic silicas and for that purpose should be used only with the hydrophilic silicas.

At present, the silica-pcm composition preferred for use includes a hydrophobic silica and alkyl hydrocarbon pcm wherein the pcm is present in an amount of 50-80 wt. % of the silica/pcm mix.

It is noted that the ultra-fine hydrophilic silica may also be used with water and used above the melting point-freezing point (0° C.) so that the water can supply both its latent and sensible heat characteristics to the desired object.

It is to be understood that thermal insulation materials such as polyurethane or polystyrene foam are desirably used to surround the shrouded pcm/silica composites in order to minimize undesirable heat loss or gain from the environment. For example, insulating materials would be used when the pcm/silica composites are used as medical wraps, tree wraps, tableware products, garments and blankets and the like. In each case, a layer of such thermal insulation would be provided so as to minimize heat loss or gain as the case may be.

In accordance with the patent statutes, the best mode of practicing the invention has been set forth. However, it will be apparent to those skilled in the art that many other modifications can be made without departing from the invention herein disclosed and described, the scope of the invention being limited only by the scope of the attached claims.

I claim:

1. A food receptacle or beverage container receptacle comprising a housing, and a powder-like mix consisting essentially of a phase change material and finely divided silica particles, in combination, disposed in said housing, said silica particles having particle sizes of about $7 \times 10^{-3}$ to about $7 \times 10^{-2}$ microns, said phase change material being selected from the group consisting of water, glycerine, ethylene glycol, crystalline alkyl hydrocarbons having a carbon chain length of $C_{14}$ and greater, crystalline fatty acids, crystalline fatty acid esters, crystalline alicyclic hydrocarbons, crystalline aromatic compounds, hydrated salts, clathrates, semi-clathrates, gas clathrates, polyethylene glycol, and halogen-terminated alkyl hydrocarbons, said phase change material having a melting and freezing point of from about $-20°$ to about 80° C. and being present in an amount of 80% or less by weight and said silica particles being present in an amount of 20% or more by weight based on the total weight of the combination of phase change material and silica particles.

2. A food receptacle or beverage container receptacle as recited in claim 1 wherein said silica particles have a surface area of between about 50 $m^2/g$ to about 500 $m^2/g$.

3. A food receptacle or beverage container receptacle as recited in claim 1 wherein said silica particles are selected from the group consisting of fumed and precipitated silicas.

4. A food receptacle or beverage container receptacle as recited in claim 1 wherein said silica particles are hydrophilic precipitated silica particles or hydrophobic silica particles.

5. A food receptacle or beverage container receptacle as recited in claim 1 wherein said phase change material is present in an amount of 50-80 wt. % based upon the combined weight of said phase change material and said silica particles.

6. A food receptacle or beverage container receptacle as recited in claim 1 further comprising a polar compound present in an amount of 5-25 wt. % based on the total weight of said silica, said phase change material and said polar compound, and wherein said receptacle may be heating by microwave energy.

7. A food receptacle or beverage container receptacle as recited in claim 1 wherein said phase change material comprises a polar phase change material compound and wherein said receptacle may be heated by microwave energy.

8. A food receptacle or beverage container receptacle as recited in claim 7 wherein said polar phase change material is chosen from the group consisting of water, glycerine, ethylene glycol, polyethylene glycol having a molecular weight of about 1,000 or greater, clathrates, semi-clathrates, gas clathrates, and hydrated salts.

9. A food receptacle or beverage container receptacle as recited in claim 1 wherein said phase change material is water.

10. A food receptacle or beverage container receptacle as recited in claim 1 wherein said phase change material comprises a crystalline alkyl hydrocarbon having a carbon chain length of $C_{14}$ and greater.

* * * * *